United States Patent [19]

Gall

[11] 4,001,261
[45] Jan. 4, 1977

[54] PROCESS FOR THE PRODUCTION OF 1-[(DIMETHYLAMINO)METHYL]-6-PHENYL-4H-IMIDAZO[1,2-a][1,4]-BENZODIAZEPINE

[75] Inventor: Martin Gall, Kalamazoo, Mich.
[73] Assignee: The Upjohn Company, Kalamazoo, Mich.
[22] Filed: Oct. 20, 1975
[21] Appl. No.: 623,971
[52] U.S. Cl. .................... 260/296 T; 424/263; 424/273
[51] Int. Cl.² ............. C07D 213/02; C07D 487/04
[58] Field of Search ................ 260/296 T, 309

[56] References Cited
UNITED STATES PATENTS 3,910,946  10/1975  Gall .................................. 260/309

OTHER PUBLICATIONS

Schreiber et al., Angew. Chem. Internat. Edit., vol. 10, pp. 330 to 331, (1971).

Masui et al., Chemical Abstracts, vol. 72, Abst. No. 78250n, (1970).

*Primary Examiner*—John D. Randolph
*Attorney, Agent, or Firm*—Hans L. Berneis

[57] ABSTRACT

A process for the preparation of 1-[(dimethylamino)-methyl]-6-substituted-4H-imidazo[1,2-a][1,4]benzodiazepine which comprises the reaction of a 6-phenyl-4H-imidazo-[1,2-a][1,4]benzodiazepine with the reagent

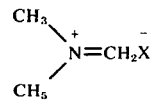

wherein X⁻ signifies the anion of a monovalent acid.

7 Claims, No Drawings

PROCESS FOR THE PRODUCTION OF 1-[(DIMETHYLAMINO)METHYL]-6-PHENYL-4H-IMIDAZO[1,2-A][1,4]-BENZODIAZEPINE

BACKGROUND OF THE INVENTION

FIELD OF THE INVENTION

This invention is directed to a novel and improved chemical process and is particularly concerned with the production of the anxiolytic 1-[(dimethylamino)methyl]-6-phenyl-4H-imidazo[1,2-a][1,4]benzodiazepines.

The process of this invention can be illustratively represented as follows:

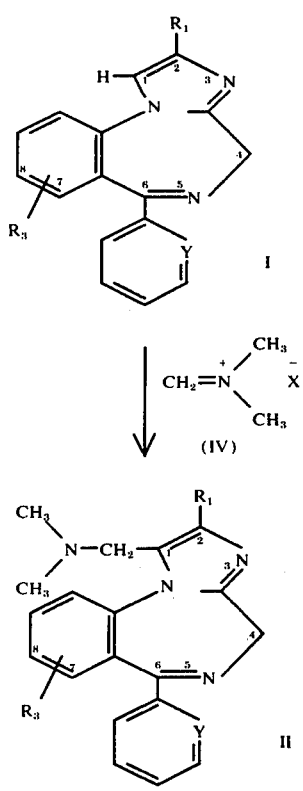

wherein $R_1$ is hydrogen or alkyl of 1 to 3 carbon atoms, inclusive; wherein Y is nitrogen or C-$R_2$ in which $R_2$ is hydrogen, chloro, or fluoro; wherein $R_3$ is hydrogen, fluoro, chloro, bromo, trifluoromethyl, or nitro; and wherein $X^-$ is the anion of a monovalent organic or inorganic acid, preferably the anions of hydrochloric, hydrobromic, and hydriodic and trifluoroacetic acid.

The novelty of this invention consists in using specific conditions with a specific reagent while applying a Mannich Type reaction to prepare as the major product compound of formula II. The use of Mannich reaction in this area is not new. Application Ser. No. 387,761, published Jan. 28, 1975, discloses the use of the Mannich reaction for the addition of a aminoalkyl group to a triazole ring. When the conditions of this disclosure are applied to the compounds of formula I of this invention the desired products of formula I are not obtained, but instead compounds of the formula III.

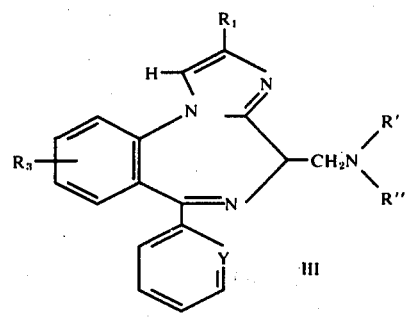

Only with the present reagent IV and the conditions further on described the compounds of formula II are obtained. The reagent used has the formula IV;

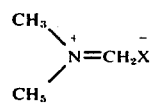

wherein $X^-$ is any suitable anion of a monovalent inorganic or organic acid such as hydrochloric, hydrobromic, hydriodic, trifluoroacetic, acetic, tetrafluoroboric, benzoic, $HPF_6$, perchloric, chloric, $HSbCl_6$ and the like. Such reagents are disclosed in the art, e.g. Böhme, H., et al., Chem. Ber. 105, 2233, (1972); Böhme, H., et al., Chem. Ber. 93, 1305 (1960), Böhme, H., Tetrahedron Lett. 2785 (1972); Volz, H. and Kiltz, H., Tetrahedron Lett. 1917 (1970) and Am. Chem. 752, 86 (1971); Huisgen, R., Kolbeck, W. Tetrahedron Lett. 783 (1965); Ahond, A. et al., J. Amer. Chem. Soc., 90, 5622 (1968); Jaser, Y., Chem. Comm. 253 (1974); Eschenmoser, A., et al., Angew. Chem. Int. Ed. (Eng) 10, 330, (1971).

In order to obtain a high yield in the reaction I → II specific reaction conditions must be applied. Under other conditions, the above described reagents can add at the 4-position only, or simultaneously in the 1- and 4-positions of compound I, thus providing products of lesser interest than those defined by formula II.

The present process is a considerable improvement over the process disclosed in application Ser. No. 505,342, filed Sept. 12, 1974, now U.S. Pat. No. 3,910,946.

In this patent the basic diazepine compound A is used to prepare a compound of formula II. This compound A has the generic structure.

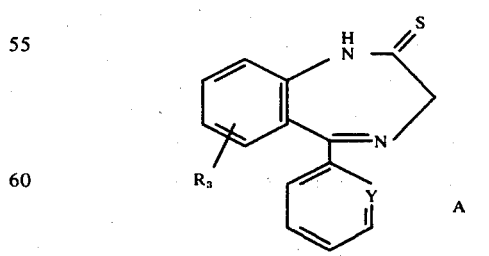

wherein Y and $R_3$ have the same significance as in formula I.

Using the procedure of the above mentioned patent, 4 steps are necessary to obtain the corresponding compound of formula II above, in an overall yield of 11.7% (in II

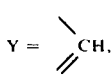

(R$_2$ is 8-chloro). In addition a reagent is necessary, which is not commercially available and, as shown in the patent, requires 5 steps to be prepared. This reagent is of the formula B;

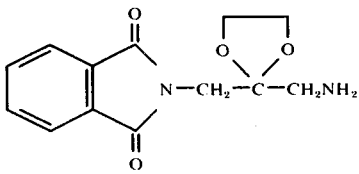

In the present process compound II (R$_3$ is 8-chloro, Y is CH) is prepared from the corresponding compound A (R$_2$ is 8-chloro) in 3 steps in an overall yield of 24% or better, with all reagents being commercially available.

In order to obtain a high yield in this reaction specific reaction conditions must be applied. Under other conditions, Bohme's reagent can add at the 4-position or in 1- and 4-positions of compound I providing products of lesser interest than those defined by formula II.

PREFERRED EMBODIMENT OF THE INVENTION

In this invention the alkyl group of 1 to 3 carbon atoms includes methyl, ethyl, propyl, and isopropyl. The preferred products of formula II are those in which R$^1$ is H and the substituent R$_3$ is in the 8-position.

The products of formula II of this invention are compounds which possess sedative and tranquilizing activity as disclosed in great detail in application Ser. No. 505,342, filed Sept. 12, 1974, now U.S. Pat. No. 3,910,946.

They are particularly useful in the treatment of mammals, including man, to alleviate anxieties and tension in oral or injectable dosages of 0.2 to 25 mg./kg. or preferredly 0.5 to 10 mg./kg.

In carrying out the process of the present invention compound of the formula I is treated with a compound of the formula IV under special and very limited conditions explained herein below:

1. The solvent may be dimethylformamide, dimethylacetamide, N-methyl pyrrolidone. The more preferred solvent is dimethylformamide. The presence of acids or bases or the use of other solvents does not leach to the formation of the desired product; rather products of structure III are formed:

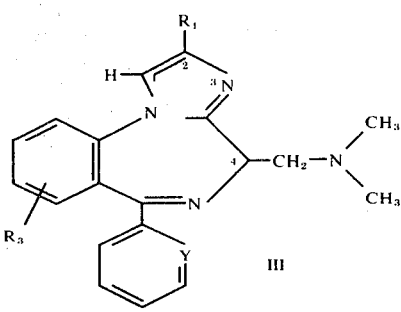

2. The yield depends on the temperature and time allowed for the reaction.

The highest yield (32%) of the desired product was obtained by stirring the reaction mixture for 72 hours at 55° to 59° C. Stirring at 100° C. for 3 hours and then at 25° C. for 20 hours gave 20% of the theoretical amount. No desired product was obtained when the reaction mixture was stirred in the presence of "proton sponge" or gaseous hydrogen chloride.

Thus the experimental conditions, besides the specific solvent dimethylformamide, requires that the reaction is carried out between 50° to 100° C. during ½ to 100 hours.

Furthermore, it was discovered that the higher yields are obtained when the time of reaction is increased and when the temperature of the reaction is decreased.

The following preparations and examples illustrate this invention, but should not be construed as limiting.

PREPARATION 1

[[7-Bromo-5-(2-pyridyl)-3H-1,4-benzodiazepine-2-yl]amino]-acetyldehyde, dimethyl-acetal A suspension of 15 g. (45 mmol) of 7-bromo-5-(2-pyridyl)[1,4]benzodiazepine-2-thione and 12 g. (114 mmol) of aminoacetaldehyde dimethyl acetal in 500 ml. of n-butanol is heated to reflux for 4 hours with a stream of nitrogen bubbling through the reaction. Within 1 hour, all solids dissolved. The solvent is removed in vacuo and the residue taken up in chloroform. The chloroform solution is washed with water and brine, dried over sodium sulfate and concentrated to a yellow brown oil in vacuo. On trituration with ethyl acetate 16.5 g. (91%) of product is obtained.

Anal. calcd. for $C_{18}H_{19}BrN_4O_2$, mw 403.27: C, 53.61; H, 4.75; N, 13.90; Br, 19.81. Found: C, 53.61; H, 4.70; N, 13.75; Br, 19.83.

PREPARATION 2

8-Bromo-6-(2-pyridyl)-4H-imidazo[1,2-a]-[1,4]benzodiazepine

A solution of 15 g. (37 mmol) of [[7-bromo-5-(2-pyridyl)-3H-1,4-benzodiazepine-2-yl]amino]acetaldehyde, dimethyl-acetal in 50 ml. of concentrated sulfuric acid, is allowed to stir at room temperature under nitrogen overnight, poured onto crushed ice and crystallized with an aqueous sodium hydroxide solution. After the product is extracted with chloroform the chloroform extract is washed with brine, dried over sodium sulfate and concentrated to an oil in vacuo. On trituration, with ethyl acetate 10.2 g. (81%) of yellow crystalline 8-bromo-6-(2-pyridyl)-4H-imidazo[1,2-a][1,4]benzodiazepine of melting point 208°–210° C. is obtained.

Anal. calcd. for $C_{16}H_{11}BrN_4$: C, 56.65; H, 3.27; N, 16.56; Br, 23.56. Found: C, 56.34; H, 3.22; N, 16.47; Br, 23.54.

EXAMPLE 1

1-(Dimethylamino)methyl-8-chloro-6-phenyl-4H-imidazo[1,2-a][1,4]benzodiazepine

1. Preparation of the reagent dimethylaminomethylene ammonium chloride.

A solution of 4.08 g. (40.0 mmol) of bis(dimethylamino)ethane in 50 ml. of dimethylformamide is treated at 0° C., with 2.824 ml. (40.0 mmol) of acetyl chloride to give a solution of dimethylmethylene ammonium chloride.

2. To this solution is added 5.86 g. (20 mmol) of 8-chloro-6-phenyl-4H-imidazo[1,2-a][1,4]benzodiazepine The mixture is heated in an oil bath between 55°–59° C. for 72 hours, quenched on ice, neutralized with a 10% aqueous sodium hydroxide solution and chromatographed over 500 g. of silica gel by eluting with 1 liter of 3% methanol/chloroform mixtures to give 2.25 g. (32%) of 1-(dimethylamino)methyl-8-chloro-6-phenyl-4H-imidazo-[1,2-a][1,4]benzodiazepine of melting point 183°–185° C.

Anal. calcd. for $C_{23}H_{26}ClN_5$: C, 67.71; H, 6.42; N, 17.17; Cl, 8.69; Found: C, 67.84; H, 6.43; N, 17.17; Cl, 8.69.

EXAMPLE 2

1-[(Dimethylamino)methyl]-8-chloro-6-(o-chlorophenyl)-4H-imidazo[1,4]benzodiazepine dihydrobromide salt.

In the manner given in Example 1, 6.56 g. (20.0 mmol) of 8-chloro-6-phenyl-4H-imidazo[1,2-a][1,4]benzodiazepine is added to a solution of dimethylmethylene ammonium trifluoroacetate [Ahond et al. J. Am. Chem. Soc. 90, 5622 (1968)] and heated for 100 hours from 55°–60° C. The mixture is quenched on ice, neutralized with a 10% aqueous sodium hydroxide solution and chromatographed over 50.0 g. of silica gel by eluting with 1 l. of a 3% methanol/97% chloroform mixture to afford 8-chloro-1-[(dimethylamino)methyl]-6-(o-chlorophenyl)-4H-imidazo-[1,2-a][1,4]benzodiazepine which crystallizes as a dihydrobromide salt, m. p. 199°–201° C.

The free compound can be obtained by treating the salt with a base, e.g. aqueous sodium hydroxide, sodium bicarbonate or carbonate, or the corresponding analogous potassium compounds.

Anal. calcd. for $C_{20}H_{18}Cl_2N_4 \cdot 1½$ HBr: C, 47.41; H, 3.88; N, 11.06; Found: C, 47.51; H, 3.98; N, 11.31.

EXAMPLE 3

1-(Dimethylamino)methyl-2-methyl-8-chloro-6-(o-chlorophenyl)-4H-imidazo[1,2-a][1,4]benzodiazepine In the manner given in Example 1, 6.844 (20 mmol) of 2-methyl-8-chloro-6-(o-chlorophenyl)-4H-imidazo[1,2-a]-[1,4]benzodiazepine is treated with 40.0 mmol of dimethylmethylene ammonium chloride in dimethylformamide during 2 hours at 100° C. The reaction mixture is quenched on ice, neutralized with 10% aqueous sodium hydroxide and chromatographed over silica gel with 1 l. fractions of 3% methanol/97% chloroform solutions to give 1-(dimethylamino)methyl-2-methyl-8-chloro-6-(o-chlorophenyl)-4H-imidazo[1,2-a][1,4]benzodiazepine of melting point 191°–194° C.

Anal. calcd. for $C_{21}H_{20}Cl_2N_4$, mw, 399.31: C, 63.16; N, 5.05; N, 14.03; Cl, 17.76. Found: C, 63.47; H, 5.09; N, 14.19; Cl, 17.69.

EXAMPLE 4

1-(Dimethylamino)methyl-8-bromo-6-(2-pyridyl)-4H-imidazo[1,2-a][1,4]benzodiazepine A solution of 0.51 g. (5.0 mmol) of $[(CH_3)_2N]_2CH_2$ in 10 ml. of dimethylformamide is cooled to 0° C. and stirred for 10 minutes. To this solution, 0.355 ml. (0.39 g., 5.0 mmol) of acetyl chloride is added dropwise over a period of 15 minutes under a nitrogen atmosphere to give dimethylmethylene ammonium chloride.

To a suspension of this reagent in 10 ml. of dimethylformamide is added 1.0 g. (3.00 mmol) of 8-bromo-6-(2-pyridyl)-4H-imidazo[1,2-a][1,4]benzodiazepine. The mixture is heated on a steam bath for a total of 2 hours, then quenched in cold water, neutralized with a 10% aqueous sodium hydroxide solution and extracted with chloroform. The chloroform layer is washed with water and brine, dried over anhydrous sodium sulfate and concentrated in vacuo to an oil, which is chromatographed over 100 g. of silica gel by eluting with 3% methanol/97% chloroform mixtures. The product is collected and crystallized from ethyl acetate to afford 150 mg. of 1-(dimethylamino)methyl-8-bromo-6-(2-pyridyl)-4H-imidazo-[1,2-a][1,4]benzodiazepine of melting point 200°–202° C.

Anal. calcd. for $C_{19}H_{18}BrN_5$, mw 396.28: C, 57.58; H, 4.58; N, 17.68; Br, 20.16. Found: C, 57.50; H, 4.32; N, 17.26; Br, 20.63.

EXAMPLE 5

8-Fluoro-1-[(dimethylamino)methyl]-6-(o-chlorophenyl)-4H-imidazo[1,2-a][1,4]benzodiazepine In the manner given in Example 1, 8-fluoro-6-(o-chlorophenyl)-4H-imidazo[1,2-a][1,4]benzodiazepine is treated with dimethylmethylene ammonium chloride to give 8-fluoro-1-[(dimethylamino)methyl]-6-(o-chlorophenyl)-4H-imidazo[1,2-a][1,4]benzodiazepine.

EXAMPLE 6

8-Chloro-[(dimethylamino)methyl]-2-methyl-6-(2-pyridyl)-4H-imidazo[1,2-a][1,4]benzodiazepine In the manner given in Example 5, 8-chloro-2-methyl-6-(2-pyridyl)-4H-imidazo[1,2-a][1,4]benzodiazepine is treated with dimethylmethylene ammonium chloride to give 8-chloro-2-methyl-6-(2-pyridyl)-4H-imidazo[1,2-a][1,4]-benzodiazepine.

EXAMPLE 7

8-Chloro-1-[(dimethylamino)methyl]-6-(o-chlorophenyl)-4-methyl-4H-imidazo[1,2-a][1,4]benzodiazepine In the manner given in Example 1, 8-chloro-6-(o-chlorophenyl)-4-methyl-4H-imidazo[1,2-a][1,4]benzodiazepine is treated with dimethylmethylene ammonium chloride to give 8-chloro-1-[(dimethylamino)methyl]-6-(o-chlorophenyl)-4-methyl-4H-imidazo[1,2-a][1,4]benzodiazepine.

EXAMPLE 8

8-Fluoro-1-[(dimethylamino)methyl]-6-(2-pyridyl)-4H-imidazo[1,2-a][1,4]benzodiazepine In the manner given in Example 5, 8-fluoro-6-(2-pyridyl)-4H-imidazo[1,2-a][1,4]benzodiazepine is treated with dimethylmethylene ammonium chloride to give 8-fluoro-6-(2-pyridyl)-4H-imidazo[1,2-a][1,4]benzodiazepine.

EXAMPLE 9

8-Fluoro-1-[(dimethylamino)methyl]-6-phenyl-4H-imidazo[1,2-a][1,4]benzodiazepine In the manner given in Example 1, 8-fluoro-6-phenyl-4H-imidazo[1,2-a][1,4]benzodiazepine is treated with dimethylmethylene ammonium chloride to give 8-fluoro-1-[(dimethylamino)methyl]-6-phenyl-4H-imidazo[1,2-a]-[1,4]benzodiazepine.

EXAMPLE 10

8-Trifluoromethyl-1-[(dimethylamino)methyl]-6-(2-pyridyl)-4H-imidazo[1,2-a][1,4]benzodiazepine In the manner given in Example 5, 8-trifluoromethyl-6-(2-pyridyl)-4H-imidazo[1,2-a][1,4]benzodiazepine is treated with dimethylmethylene ammonium chloride to give 8-trifluoromethyl-6-(2-pyridyl)-4H-imidazo[1,2-a][1,4]-benzodiazepine.

EXAMPLE 11

8-Bromo-1-[(dimethylamino)methyl]-6-(o-chlorophenyl)-4H-imidazol[1,2-a][1,4]benzodiazepine In the manner given in Example 1, 8-bromo-6-(o-chlorophenyl)-4H-imidazo[1,2-a][1,4]benzodiazepine is treated with dimethylmethylene ammonium chloride to give 8-bromo-1-[(dimethylamino)methyl]-6-(o-chlorophenyl)-4H-imidazo[1,2-a][1,4]benzodiazepine.

EXAMPLE 12

8-Nitro-1-[(dimethylamino)methyl]-6-(o-chlorophenyl)-4H-imidazo[1,2-a][1,4]benzodiazepine In the manner given in Example 1, 8-nitro-6-(o-chlorophenyl)-4H-imidazo[1,2-a][1,4]benzodiazepine is treated with dimethylmethylene ammonium chloride to give 8-nitro-1-[(dimethylamino)methyl]-6-(o-chlorphenyl)-4H-imidazo[1,2-a][1,4]benzodiazepine.

EXAMPLE 13

8-Chloro-1-[(dimethylamino)methyl]-6-(o-fluorophenyl)-4H-imidazo[1,2-a][1,4]benzodiazepine In the manner given in Example 1, 8-chloro-6-(o-fluorophenyl)-4H-imidazo[1,2-a][1,4]benzodiazepine is treated with dimethylmethylene ammonium chloride to give 8chloro-1-[(dimethylamino)methyl]-6-(o-fluorophenyl)-4H-imidazo[1,2-a][1,4]benzodiazepine.

EXAMPLE 14

1-[(Dimethylamino)methyl]-6-(o-chlorophenyl)-4H-imidazo[1,2-a][1,4]benzodiazepine In the manner given in Example 1, 6-(o-chlorophenyl)-4H-imidazo[1,2-a][1,4]benzodiazepine is treated with dimethylmethylene ammonium chloride to give 1-[(dimethylamino)methyl]-6-(o-chlorophenyl)-4H-imidazo[1,2-a][1,4]-benzodiazepine.

EXAMPLE 15

1-[(Dimethylamino)methyl]-2-methyl-6-(2-pyridyl)-4H-imidazo[1,2-a][1,4]benzodiazepine In the manner given in Example 5, 6-(2-pyridyl)-4H-imidazo[1,2-a][1,4]benzodiazepine is treated with dimethylmethylene ammonium chloride to give 6-(2-pyridyl)-4H-imidazo[1,2-a][1,4]benzodiazepine.

EXAMPLE 16

8-Trifluoromethyl-1-[(dimethylamino)methyl]-6-(o-chlorophenyl)-4H-imidazo[1,2-a][1,4]benzodiazepine In the manner given in Example 1, 8-trifluoromethyl-6-(o-chlorophenyl)-4H-imidazo[1,2-a][1,4]benzodiazepine is treated with dimethylmethylene ammonium chloride to give 8-trifluoromethyl-1-[(dimethylamino)methyl]-6-(o-chlorophenyl)-4H-imidazo[1,2-a][1,4]benzodiazepine.

EXAMPLE 17

7-Chloro-1-[(dimethylamino)methyl]-6-phenyl-4H-imidazo[1,2-a][1,4]benzodiazepine In the manner given in Example 1, 7-chloro-6-phenyl-4H-imidazo[1,2-a][1,4]benzodiazepine is treated with dimethylmethylene ammonium chloride to give 7-chloro-1-[(dimethylamino)methyl]-6-phenyl-4H-imidazo[1,2-a][1,4]benzodiazepine.

EXAMPLE 18

7-Bromo-1-[(dimethylamino)methyl]-2-ethyl-6-(2-pyridyl)-4H-imidazo[1,2-a][1,4]benzodiazepine In the manner given in Example 5, 7-bromo-2-ethyl-6-(2-pyridyl)-4H-imidazo[1,2-a][1,4]benzodiazepine is treated with dimethylmethyleneammonium chloride to give 7-bromo-1-[(dimethylamino)methyl]-2-ethyl-6-(2-pyridyl)-4H-imidazo[1,2-a][1,4]benzodiazepine.

By the same process given in the preceeding examples other 1-[(dimethylamino)methyl]-6-(substituted)-4H-imidazo-[1,2-a][1,4]benzodiazepines can be produced e.g.

9-trifluoromethyl-1-[(dimethylamino)methyl]-6-phenyl-4H-imidazo[1,2-a][1,4]benzodiazepine;
10-fluoro-1-[(dimethylamino)methyl]-6-(o-chlorophenyl)-4H-imidazo[1,2-a][1,4]benzodiazepine;
10-bromo-1-[(dimethylamino)methyl]-6-(o-fluorophenyl)-4H-imidazo[1,2-a][1,4]benzodiazepine;
9-chloro-1-[(dimethylamino)methyl]-6-(2,6-difluorophenyl)-4H-imidazo[1,2-a][1,4]benzodiazepine;
10-nitro-1-[(dimethylamino)methyl]-6-phenyl-4H-imidazo[1,2-a][1,4]benzodiazepine;
7-nitro-1-[(dimethylamino)methyl]-6-phenyl-4H-imidazo[1,2-a][1,4]benzodiazepine;
8-chloro-1-[(dimethylamino)methyl]-4-ethyl-6-(o-chlorophenyl)-4H-imidazo[1,2-a][1,4]benzodiazepine;
7-bromo-1-[(dimethylamino)methyl]-4-methyl-6-phenyl-4H-imidazo[1,2-a][1,4]benzodiazepine;
10-trifluoromethyl-1-[(dimethylamino)methyl]-4-ethyl-6-phenyl-4H-imidazo[1,2-a][1,4]benzodiazepine;
9-bromo-1-[(dimethylamino)methyl]-4-methyl-6-phenyl-4H-imidazo[1,2-a][1,4]benzodiazepine;
9-nitro-1-[(dimethylamino)methyl]-2,4-dimethyl-6-(o chlorophenyl)-4H-imidazo[1,2-a][1,4]benzodiazepine;

1-[(dimethylamino)methyl]-2-ethyl-6-(o-chloro-
phenyl)-4H-imidazo[1,2-a][1,4]benzodiazepine;
10-trifluoromethyl-1-[(dimethylamino)methyl]-6-(2-
pyridyl)-4H-imidazo[1,2-a][1,4]benzodiazepine;
9-bromo-1-[(dimethylamino)methyl]-6-(2-pyridyl)-
4H-imidazo[1,2-a][1,4]benzodiazepine;
10-bromo-1-[(dimethylamino)methyl]-6-(2-pyridyl)-
4H-imidazo[1,2-a][1,4]benzodiazepine;
9-fluoro-1-[(dimethylamino)methyl]-2-methyl-6-(2-
pyridyl)-4H-imidazo[1,2-a][1,4]benzodiazepine;
7-trifluoromethyl-1-[(dimethylamino)methyl]-2-ethyl-
6-(2-pyridyl)-4H-imidazo[1,2-a][1,4]benzodiaze-
pine;
7-nitro-1-[(dimethylamino)methyl]-2-methyl-6-(2-
pyridyl)-4H-imidazo[1,2-a][1,4]benzodiazepine;
9-nitro-1-[(dimethylamino)methyl]-2,4-dimethyl-6-(2-
pyridyl)-4H-imidazo[1,2-a][1,4]benzodiazepine;

and the like.

I claim:

1. A process for the production of 1-[(dime-thylamino)-methyl]-6-substituted-4H-imidazo[1,2-a][1,4]benzodiazepines of the formula II:

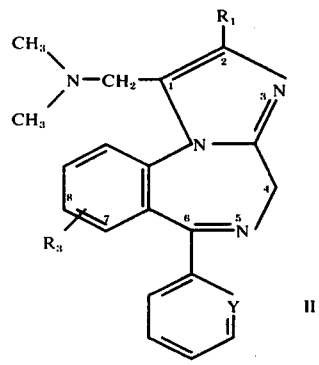

II wherein $R_1$ is hydrogen or alkyl of 1 or 2 carbon atoms, inclusive; wherein Y is nitrogen or C-$R_2$ in which $R_2$ is hydrogen, fluoro, or chloro; and wherein $R_3$ is hydrogen, fluoro, chloro, bromo, trifluoromethyl; which comprises:

treating a compound of formula I:

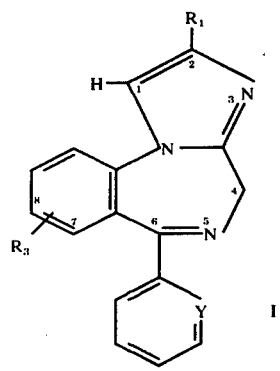

I wherein $R_1$, Y and $R_3$ are defined as above, in solution between 50°–100° C. with a compound of formula IV

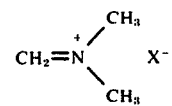

wherein $X^-$ is the anion of monovalent inorganic or organic acid to yield the corresponding compound of formula II.

2. The proess of claim 1, wherein the compound of formula IV is

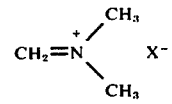

wherein $X^-$ is the anion of hydrochloric, hydrobromic, hydriodic or trifluoroacetic acid.

3. The process of claim 1, wherein the preferred starting product I has the substituent $R_3$ in the 8-position and $R_1$ is hydrogen.

4. The process of claim 2, wherein the preferred starting compound has the substituent $R_3$ in the 8-position and $R_1$ is hydrogen.

5. The process of claim 1, wherein the starting compound is selected from the group consisting of 8-chloro-6-phenyl-2-methyl-4H-imidazo[1,2-a][1,4]benzodiazepine; 8-chloro-6-(-o-chlorophenyl)-4H-imidazo-[1,2-a][1,4]benzodiazepine; 8-chloro-6-(o-chlorophenyl)-2-methyl-4H-imidazo[1,2-a][1,4]benzodiazepine; and 8-bromo-6-(2-pyridyl)-4H-imidazo[1,2-a][1,4]benzodiazepine.

6. A process for the production of 8-chloro-1-[(dimethylamino)methyl]-6-phenyl-4H-imidazo[1,2-a][1,4]-benzodiazepine which comprises: treating

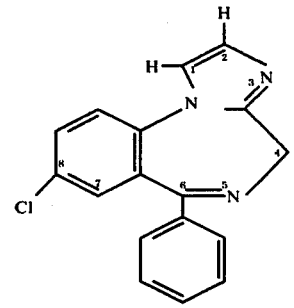

in dimethylformamide at 50° to 100° C. with

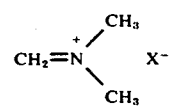

wherein $X^-$ is the anion of hydrochloric, hydrobromic, hydriodic or trifluoroacetic acid.

7. The process of claim 6, wherein the temperature of the reaction is between 50° to 60° C.

* * * * *